United States Patent [19]

Hofmann et al.

[11] Patent Number: 4,656,157
[45] Date of Patent: Apr. 7, 1987

[54] MOLDED CATALYST FOR REACTIONS CARRIED OUT UNDER HETEROGENEOUS CATALYSIS

[75] Inventors: Friedbert Hofmann, Neuhofen; Richard Krabetz, Kirchheim; Matthias Schwarzmann, Limburgerhof, all of Fed. Rep. of Germany

[73] Assignee: BASF Aktiengesellschaft, Fed. Rep. of Germany

[21] Appl. No.: 803,638

[22] Filed: Dec. 2, 1985

[30] Foreign Application Priority Data

Dec. 12, 1984 [DE] Fed. Rep. of Germany ....... 3445289

[51] Int. Cl.$^4$ .............................................. B01J 35/02
[52] U.S. Cl. ..................................... 502/439; 502/527
[58] Field of Search ................................ 502/439, 527

[56] References Cited

U.S. PATENT DOCUMENTS 2,408,164  9/1946  Foster .................................. 502/527
3,898,180  8/1975  Crooks et al. .................. 502/527 X
3,966,644  6/1976  Gustafson et al. ............. 502/527 X
4,366,093  12/1982  Shiozaki et al. ..................... 502/439

FOREIGN PATENT DOCUMENTS 0008424  8/1979  European Pat. Off. .
3346259  6/1984  Fed. Rep. of Germany .
2133307  7/1984  United Kingdom .

Primary Examiner—W. J. Shine
Attorney, Agent, or Firm—Keil & Weinkauf

[57] ABSTRACT

A molded catalyst for reactions carried out under heterogeneous catalysis consists of a catalytically active material shaped into hollow cylinders, or of an inert carrier which is shaped into hollow cylinders and onto which catalytically active material is applied the external diameter of the hollow cylinders being from 3 to 20 mm, the internal diameter being from 0.1 to 0.7 times the external diameter and the length being from 0.2 times to twice the external diameter. The end faces of the hollow cylinder are curved so that the radius of curvature is from 0.4 to 5 times the external diameter.

The novel catalysts are particularly useful for partial oxidation in the gas phase.

2 Claims, 2 Drawing Figures

MOLDED CATALYST FOR REACTIONS CARRIED OUT UNDER HETEROGENEOUS CATALYSIS

The present application relates to a molded catalyst for reactions carried out under heterogeneous catalysis, as employed, for example, in the form of fixed beds for gas-phase or liquid-phase reactions.

It is an object of the present invention to provide catalysts which are preferably used for exothermic or endothermic reactions which lead to more than one product, so that the selective conversion of the raw materials to a particular product is of critical importance. For optimum temperature control, such reactions, in particular gas-phase ones, must be carried out in reactors having a large internal heat exchange area, for example tube bundle reactors, in order to effect rapid removal or supply of heat of reaction and thus avoid the formation of large local temperature differences in the catalyst bed and consequently the formation of undesirable by-products.

A large variety of shapes are known for fixed bed catalysts, for example spheres, solid and hollow cylinders, stars, spoked wheels and honeycombs. The catalyst shapes most commonly used in practice are spheres and solid and hollow cylinders. These shapes can be produced with adequate mechanical strength by techniques which are relatively easy to master, eg. tumbling agglomeration (spheres) and tableting or extrusion to give solid or hollow cylinders. It is also known that the shape and dimensions of the catalyst particles directly or indirectly influence the pressure loss of the catalyst bed and hence the energy costs, the selectivity and the specific consumption of raw materials, which depends to a great extent on the resistance to material and heat transport in the pore structure of the catalyst moldings and on the length of the diffusion paths, and the volume activity and spacetime yield, which is determined by, inter alia, the amount of active catalyst material by unit bed volume, and the mechanical strength of the moldings and hence their life.

The effect of catalyst shape on the residence time distribution in industrial reactors, which affects both the reactor performance and the extent of side reactions, has not been taken into account to date. The residence time distribution depends on, inter alia, how uniformly in respect of a void volume and hence a pressure loss over the reactor cross-section it is possible to fill, for example, the tubes of a tube bundle reactor during the shut-down time of an industrial plant. Because of the loss of production, the shutdown time is as a rule so short that it is necessary to dispense with the time-consuming procedure of equilibrating the pressure loss in the reaction tubes. In tube bundle reactors in which the heat-transporting medium is passed through the tubes while the catalyst is introduced into the intermediate spaces, equilibration of the pressure loss over the reactor cross-section is virtually impossible.

It is also known that the less abrasion-resistant a catalyst, the more difficult it is to achieve a uniform pressure loss over the reactor cross-section.

The catalyst shapes used in practice to date have various disadvantages from the above-mentioned points of view. For example, although spheres generally have better abrasion resistance than cylinders, the greater pressure loss and the longer diffusion path and hence the poorer selectivity of spheres and solid cylinders compared with hollow cylinders of the same external diameter are disadvantages.

We have found that this object is achieved, and that the above disadvantages are avoided by a novel molded catalyst which is suitable for reactions under heterogeneous catalysis and consists of a catalytically active material shaped into hollow cylinders or of an inert carrier which is shaped into hollow cylinders and onto which a catalytically active material is applied, the external diameter of the hollow cylinders being from 3 to 20 mm, the internal diameter being from 0.1 to 0.7 times the external diameter and the length being from 0.2 times to twice the external diameter, if the end faces of the hollow cylinder are curved convexly, the radius of curvature being from 0.4 to 5, preferably 0.6 to 2 times the external diameter.

For reasons relating to manufacture, the diameter of the domes mounted on the end faces of the cylindrical part can be up to about 0.2 mm smaller than the external diameter of the cylindrical part.

BRIEF DESCRIPTION OF THE DRAWING

The shape of the catalyst can be seen from the attached drawing in which:

FIG. 1 illustrates a possible cross-section of the novel catalysts, in which 1 denotes the external diameter, 2 denotes the internal diameter, and 3 and 4 denote the end faces of the hollow cylinder and 5 denotes the radius of curvature of the end faces. FIG. 2 shows two limiting cases a and b for the novel catalysts; for a, the radius of curvature (5) of the end faces is about 0.5 times the external diameter (1) and the internal diameter (2) is 0.17 times the external diameter (1), and for b the radius of curvature of the end faces is about twice the external diameter and the internal diameter is about 0.7 times the external diameter.

Figure 1:
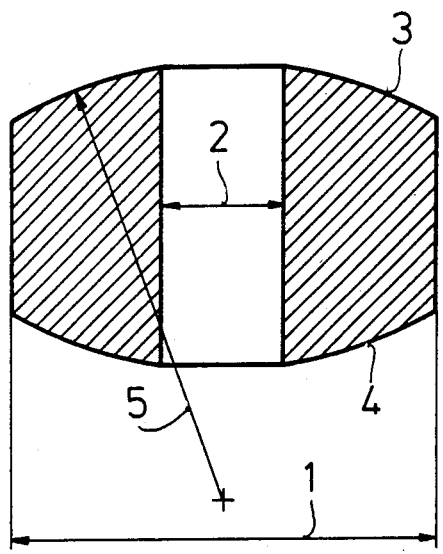
FIG. 1 is a cross-sectional view of one embodiment of the invention.

The novel catalyst shape combines the advantages of hollow cylinders with regard to selectivity with better abrasion resistance than in the case of solid and hollow cylinders, and lower flow resistance (pressure loss). Particularly surprising is the fact that, compared with the conventional hollow cylinders with flat end faces, the distribution of bulk densities or of pressure loss on filling industrial tubes is smaller. In industrial reactors, the narrow distribution gives better average selectivity and/or space-time yield.

The novel catalysts are prepared by a conventional method, for example by precipitating the oxides, hydrated oxides, hydroxides or other poorly soluble compounds of the components from solutions of their salts, or by thoroughly mixing the starting materials, in the form of the oxides and/or salts, which may be dissolved and/or suspended in water or an organic solvent and then drying the product, if required, thermally decomposing the salts, milling the product to give a suitable particle size capable of being tableted, molding to give the novel shape in a suitable tableting press and, if appropriate, then subjecting the product to heat treatment at elevated temperatures in an oxidizing, reducing or inert atmosphere. Molding assistants, such as graphite, carbon black, stearic acid, starch, polyacrylic acid, mineral oil, vegetable oil, methylcellulose, etc., and reinforcing agents, such as inorganic fibers, eg. glass fibers, asbestos fibers and the like, or inorganic powders, eg.

metal powders, metal flakes, inert carriers, eg. $SiO_2$, metal silicates and aluminum silicates, aluminas, aluminum hydroxides, aluminum oxide hydroxides, MgO, $TiO_2$, $ZrO_2$, $Nb_2O_3$, pumice, silicon carbide and magnesium silicates, may be added to the catalyst material at any stage of preparation prior to molding.

The novel catalyst shape is also advantageous for supported catalysts which are prepared by applying the active components onto the previously molded inert carrier from a solution or a suspension of the components in the oxide or salt form by impregnation, evaporation or spraying. During the production of catalysts of this type, in particular annular ones, larger or smaller amounts of the individual particles generally agglomerate, frequently via the end faces, to give twins or triplets, which often cannot be completely separated even after the production batch has been subjected to an expensive screening procedure, and therefore result in greater fluctuations in density when introduced into a reactor. In the case of the novel catalyst shape or carrier shape, the extent of agglomeration is negligible.

There are no restrictions in respect of the chemical composition of the catalysts.

The novel catalyst shape is preferably used for partial oxidation reactions in the gas phase, in particular the selective conversion of propylene to acrolein/acrylic acid, of isobutene or tert.-butyl alcohol to methacrolein/methacrylic acid and of (meth)acrolein to (meth)acrylic acid, the oxidative dehydrogenation of isobutyric acid or isobutyrates to methacrylic acid or methacrylates, respectively, the oxidation of n-butane, n-butene and benzene to maleic acid, of o-xylene to phthalic anhydride, and of toluene and substituted toluenes to substituted benzaldehydes and benzoic acids. Although there are in principle no restrictions with regard to the catalyst composition, particularly advantageous catalysts are those whose composition corresponds to the general formula:

$$Mo_aV_bW_cA_dB_eC_fD_gO_x$$

where the atoms A are one or more elements from the group consisting of Ni, Co, Fe, Bi, Cu, Rh, Ru, Re, Pd, Cr, Mn, Sn, Ce, Ag, Pb and Sb, the atoms B are one or more elements from the group consisting of P, B and As, the atoms C are one or more elements from the group consisting of the alkali metals and/or alkaline earth metals and Tl, and the atoms D are one or more elements from the group consisting of the rare earths, Nb, Ta and U, a=0-12,
b=0-12
c=0-12
a+b+c=12
d=0-12
e=0-3
f=3-3 and
g=0-12, and which may or may not be applied on inert carriers or mixed with inert carrier materials.

Active materials having this composition can generally be molded to spheres and solid and hollow cylinders having adequate compressive strength and abrasion resistance only on the loss of selectivity. These disadvantages are much less pronounced in the case of the novel catalysts.

The Examples which follow illustrate the advantages of the catalysts according to the invention over conventional catalysts in the form of hollow cylinders.

EXAMPLE 1

A catalytically active material having the composition corresponding to the formula $$Mo_{10}V_1P_1As_{0.2}Cu_{0.25}W_{0.1}K_{0.12}O_x$$

was prepared by the following method:

300 parts by weight of $MoO_3$, 18.9 parts by weight of $V_2O_5$, 24 parts by weight of 85% strength $H_3PO_4$, 5.4 parts by weight of $As_2O_5 \cdot H_2O$ and 3.3 parts by weight of CuO in 3000 parts by weight of distilled water were refluxed for 3 hours, while stirring. 1.35 parts by weight of 85% strength KOH and 8 parts by weight of phosphotungstic acid were added, after which the solution was heated at the boil for a further 3 hours. After the addition of 100 parts by weight of kieselguhr, the suspension was evaporated to dryness.

The oxide material was then milled to a particle size of less than 1.2 mm and mixed with 2% by weight of graphite powder, after which the mixture was pressed to tablets having the following dimensions:

(A) Rings having the same external and internal diameters as stated under (B). In contrast to (B), the end faces of the rings were convex the radius of curvature being 7 mm. The axial length was 5 mm (novel catalyst A). (B) Rings having an external diameter of 7 mm, an internal diameter of 3 mm and a length of 5 mm (comparative cataLyst B).

To simulate the filling process for an industrial tube bundle reactor, 0.75 kg of moldings was introduced in each case in the course of 30 sec at a constant rate into a vertical glass tube having a length of 150 cm and an internal diameter of 25 mm, and the level was then read off on a scale.

The table shows the number of filling experiments, out of 100 experiments in each case, for which the deviation of the level from the mean level was less than ±1%.

| Deviation less than | Number of experiments (tubes) for | |
|---|---|---|
| | novel catalyst A | comparative catalyst B |
| ±0.5% | 84 | 50 |
| ±1.0% | 98 | 74 |

The scatter of the levels and hence of the void volume and the pressure loss is substantially narrower in the case of the novel catalyst than in the case of the comparative catalyst.

To test the effective abrasion resistance, a catalyst charge having an initial weight of 0.75 kg was introduced 50 times into the tube, and the weight loss was determined after the dust had been removed by sieving. The weight loss is 2.4% by weight for the comparative catalyst B and, in contrast, only 1.8% by weight for the novel catalyst A.

EXAMPLE 2

Water and methylcellulose were added to a steatite material consisting of 83% by weight of soapstone, 9% by weight of plastic clay and 8% by weight of feldspar, and the mixture was pressed to give moldings A and B, which were then calcined at 1000° C.

Figure 2A:
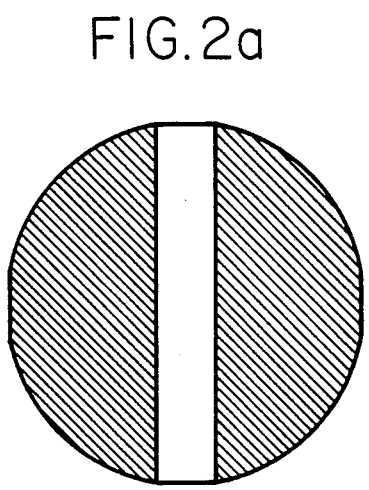
FIG. 2 sets forth two cross-sectional views of further embodiments of the invention.
Figure 2B:
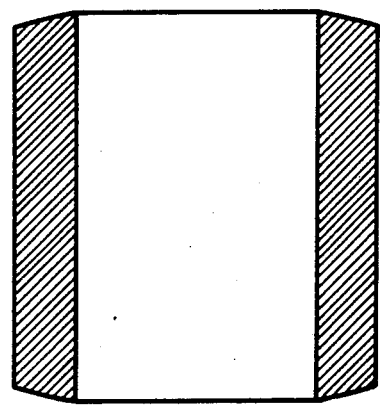

Molding A is a perforated sphere corresponding to FIG. 2a, the external diameter of the cylindrical part being 8 mm, the collar being 1 mm wide, the whole diameter being 4 mm, the length being 6 mm and the radius of curvature being 4.5 mm (carrier A). Molding B is a hollow cylinder having an external diameter of 8 mm, a length of 6 mm and an internal diameter of 4 mm (carrier B, comparative catalyst).

A catalytically active material having the composition

$$Mo_{12}NiCo_7Fe_3Bi_2B_2Sb_{0.1}K_{0.14}O_{56.7}$$

was prepared as described in Example 1 of GB-A No. 1 491 750. The material was milled to a particle size of less than 30 μm.

157 parts by weight of each of the catalytically active powders were suspended in 143 parts by weight of water, the suspension was sprayed at a rate of 0.16 kg per kg per hour onto 1000 parts by weight of carrier moldings A and B. The carriers were present in a rotating drum which revolved at a speed of 35 rpm and was heated indirectly to 40°–50° C. The suspension was sprayed through a two-material atomizer nozzle with 7.5 m³ (S.T.P.) per kg per hour of air ant 22° C. When the coating procedure was complete, the resulting coated catalysts were subsequently dried at 100° C.

The amount of agglomerated particles was less than 1% by weight in the case of catalyst A and about 5% by weight for catalyst B.

The simulation of the process for filling industrial tubes according to Example 1 and Comparative Example 1, where 680 ml of the catalysts were used in each case, gave the results summarized in Table 2.

TABLE 2

| | Deviation of the level from the mean level | |
|---|---|---|
| | Number of experiments for | |
| Deviation less than | novel catalyst A | comparative catalyst B |
| ±1.0% | 80 | 62 |
| ±1.5% | 100 | 72 |
| ±2.0% | 100 | 82 |

We claim:

1. A molded catalyst which is suitable for reactions carried out under heterogeneous catalysis and consists of a catalytically active material shaped into a hollow cylinder or of an inert carrier which is shaped into a hollow cylinder and on which a catalytically active material is applied, the external diameter of the hollow cylinder being from 3 to 20 mm, the internal diameter being from 0.1 to 0.7 times the external diameter and the length being from 0.2 times to twice the external diameter, wherein the end faces of the hollow cylinder are curved convexly, the radius of curvature being from 0.4 to 5 times the external diameter.

2. The catalyst of claim 1, wherein the radius of curvature is from 0.6 times to twice the external diameter.

* * * * *